United States Patent [19]

Siposs

[11] 4,013,074
[45] Mar. 22, 1977

[54] IMPLANTABLE MEDICATION-DISPENSING DEVICE

[76] Inventor: George G. Siposs, 2855 Velasco Lane, Costa Mesa, Calif. 92626

[22] Filed: Apr. 6, 1976

[21] Appl. No.: 674,107

Related U.S. Application Data

[63] Continuation-in-part of Ser. No. 481,886, June 21, 1974, abandoned, which is a continuation-in-part of Ser. No. 362,411, May 21, 1973, abandoned.

[52] U.S. Cl. .......................... 128/260; 128/214 F; 222/386.5
[51] Int. Cl.² .................... A61M 7/00; A61M 5/00
[58] Field of Search .......... 128/260, 214 F, 214 E, 128/DIG. 1, DIG. 13; 222/386.5

[56] References Cited
UNITED STATES PATENTS

| | | | |
|---|---|---|---|
| 2,795,245 | 6/1957 | Meehan | 141/26 |
| 3,310,051 | 3/1967 | Schulte | 128/260 X |
| 3,492,996 | 2/1970 | Fountain | 128/350 |
| 3,527,220 | 9/1970 | Summers | 128/260 |
| 3,542,022 | 11/1970 | Bartnik | 128/215 |
| 3,692,027 | 9/1972 | Ellinwood, Jr. | 128/260 |
| 3,731,681 | 5/1973 | Blackshear | 128/214 F |
| 3,923,060 | 2/1975 | Ellinwood, Jr. | 128/260 |
| 3,951,147 | 4/1976 | Tucker | 128/260 |

*Primary Examiner*—Aldrich F. Medbery
*Attorney, Agent, or Firm*—Allen A. Dicke, Jr.

[57] ABSTRACT

This invention is directed to an implantable medication-dispensing device which is arranged for subcutaneous implantation. The device has hard body in which is located a liquid reservoir, an adjacent gas chamber, and a pump which is manually operable through the cutaneous layer for drawing liquid medication from the reservoir and dispensing it and directing it into the body tissue below the hypoderm. A refill membrane permits injection of medication into the reservoir so that the implanted device can be periodically refilled.

8 Claims, 3 Drawing Figures

IMPLANTABLE MEDICATION-DISPENSING DEVICE

CROSS REFERENCE

This application is a continuation-in-part of application Ser. No. 481,886, filed June 21, 1974 now abandoned, which in turn was a continuation-in-part of patent application Ser. No. 362,411, filed May 21, 1973 now abandoned, entitled "Implantable Medication-Dispensing Device."

BACKGROUND

This invention is directed to a hard body medication-dispensing device which can be implanted into a human patient so that the medication can be dispensed from a reservoir in the body manually from the device into the patient.

The present most commonly treated chronic condition which requires periodic medication is diabetes. Over about 2 million persons in the United States take daily injections for diabetes. Whether the doctor or the patient himself applies the injection, it is painful, cumbersome, and requires preparing the proper dosage and proper sterilization. In diabetes, insulin is periodically (at least daily) subcutaneously injected to maintain the sugar balance level. Periodic tests of sugar level permit the regulation of the amount of insulin medication taken. In present practice, the daily dose is adjusted in accordance with the need for insulin. Insulin is consumed throughout the day, but the injection of insulin at a periodic rate of more than once a day is cumbersome and painful. The present method of insulin medication thus has several drawbacks: First, it is difficult to foretell in the morning what the daily usage will be; second, each medication requires injection with its pain, cumbersomeness, and infection risk; third, a large dosage of insulin is not as physiologically desirable as several small doses.

There are other chronic conditions and diseases which require medicinal drug injections. One is cystic fibrosis where, in the later stages of the disease, substantially antibiotic levels are maintained in the patient. Antidote drug-dispensing may also be successfully achieved with an implanted dispensing device. In view of this understanding, it is clear that the term "drug" is used in its broadest sense and includes all therapeutic and diagnostic agents, such as hormones, vitamins, antibiotics, anticoagulants, cancericidal and spermicidal agents, vasoactive agents, and all other substances used to control, treat, diagnose, or otherwise affect physical or mental conditions of either normal or abnormal character existing in or on an animal body. In any such circumstances, it is desirable to employ an implanted medication-dispensing device of such nature that it can be manually operated to dispense when medication is desired, or can be electrically triggered from an implanted physiological sensor.

A review of the known prior art reveals that previously available implantable medicine-dispensing devices relied upon cumbersome methods to effect release of the medication when the release signal was applied from the exterior. These methods include electromagnetic coupling of questionable operability and the like. Other implanted devices control release of the medication into the body from a timed source, with the medicine being released whether or not the patient needed it. Others, such as a Blackshear (U.S. Pat. No. 3,731,681) continuously discharge medication without any opportunity for post implantation delivery control. In the case of diabetes, the patient usually checks his blood sugar level several times daily by simple urine tests to determine the amount of insulin required. The required amount is usually injected once a day (in the morning) and thus the dosage cannot be regulated with great accuracy with respect to need throughout the day. It is more desirable to cause medication dispensing at a plurality of times during the day and in response to need, rather than time. Other previously available devices dispense solid medication or waxy substances which have to be melted by body temperature for release. There is need for a liquid-dispensing device which is capable of injecting tiny, well regulated-as-to-volume amounts (if necessary) of liquid medication.

SUMMARY

In order to aid in the understanding of this invention, it can be stated in essentially summary form that it is directed to an implanted hard-body medication-dispensing device, the performance of which is manually controlled. The device is arranged in three functional parts: There is a reservoir for maintaining the supply of liquid medication sufficient to last through a plurality of medication-dispensing periods; there is a liquid flow control device which is manually operable when the device is subcutaneously implanted to discharge medication to the tissues below the hypoderm; there is a refill means connected to the reservoir so that medication can be inserted into the reservoir so that the reservoir can be refilled.

It is thus an object of this invention to provide a medication-dispensing device which can be implanted into a patient and can be manually operated after having been so implanted. It is another object to provide an implanted medication-dispensing device wherein digital operation permits the patient to periodically dispense medicine from the device into his body tissue or fluids. It is yet another object to provide a medication-dispensing device which includes a reservoir so that manual operation of the device dispenses medication from the reservoir into the body tissue. It is yet another object to provide a manually operated implanted medication-dispensing device which has a dispenser in the device of such nature that, when the device is implanted and the dispenser operated, only a fraction of the daily dose is dispensed so that inadvertent dispensing action will not cause harmful medicinal overdose. It is yet another object to provide a medication-dispensing device of such reliable design and construction that it can operate in subcutaneous implanted position in a trouble-free manner. It is yet another object to provide a medication-dispensing device which is economic to build and easy to implant and use so that the device is economically and conveniently available to those who need it and can be implanted relatively easily, possibly under local anaesthesia.

Other objects and advantages of this invention will become apparent from a study of the following portion of the specification, the claims, and the attached drawings.

DESCRIPTION

Figure 1:
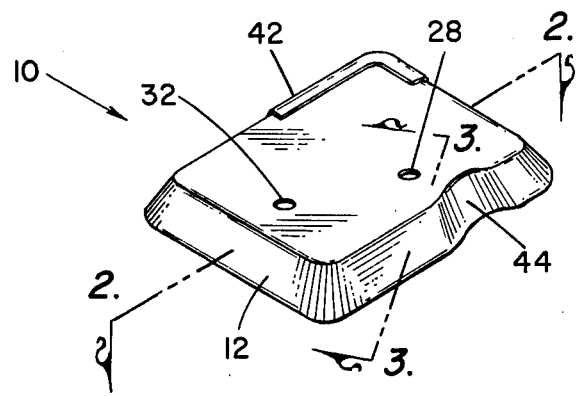
FIG. 1 is an isometric view of the manually-operated implantable medication-dispensing device of this invention.
Figure 2:
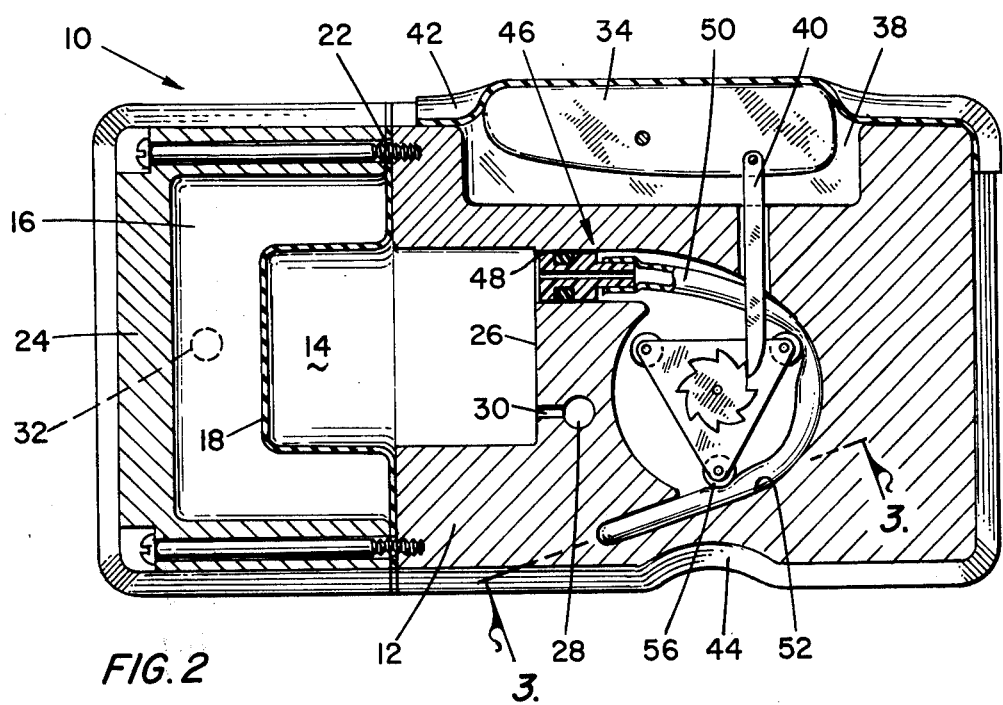
FIG. 2 is an enlarged horizontal section of the device taken generally along the line 2—2 of FIG. 1.
Figure 3:
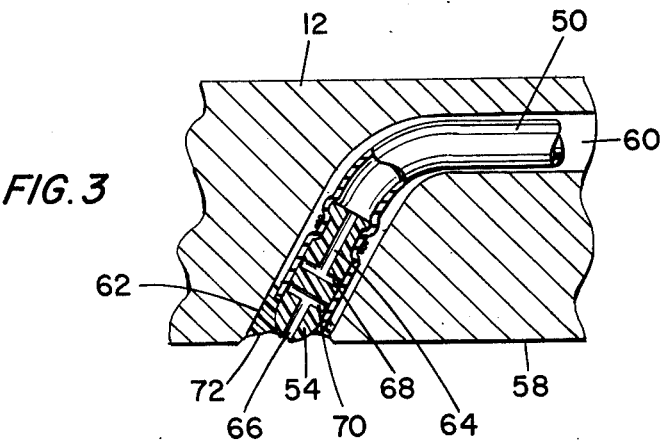
FIG. 3 is a further enlarged partial section through the device, taken generally along the line 3—3 of FIGS. 1 and 2.

The preferred embodiment of the manually-operated implantable medication-dispensing device is illustrated in FIGS. 1, 2, and 3 and is generally indicated at 10 in several of the figures. The device 10 is shown in isometric in FIG. 1, but its external configuration is exemplary and not limiting. The device 10 has an overall size of approximately the size of a pack of cigarettes. It is smoothly contoured so that it fits comfortably under the skin of the wearer and does not create voids in the tissue. A simple rectangular configuration with tapered edges is shown in the drawings for purposes of illustration, but other external shapes may be more desirable for particular circumstances. The device may be oval, circular, or of square shape, depending upon the anatomical site of implantation and the physical characteristics of the wearer. The wearer may be an adult, a child, or an animal. The materials used in the construction of the device are such that they are compatible with body tissue and with the medication used. Particular examples of suitable materials are polycarbonate such as Lexan, acrylic such as methyl methacrylate, cobalt base stainless steel, epoxy resin, Teflon, and silicone rubber. The material of body 12 is sufficiently hard or rigid that it does not substantially deflect under ordinary loads so the reservoir is protected against pressure changes or liquid discharges due to ordinary impact. This strength causes the device 10 to retain its apparent volume so that, as medication is dispensed, it does not reduce in external dimensions. Thus, there is no stress on the surrounding tissues due to volume change or device 10 due to filling of or dispensing from the device.

Reservoir 14 is separated from gas volume chamber 16 within the body of device 10 by wall 18 which is made of flexible material. Wall 18 has a flange 22 which is engaged under cap 24, which clamps the diaphragm in place. Chamber 16 is such that its volume is approximately four times the change in volume of medication in reservoir 14. Thus, with the change in volume of medication within the reservoir, the change in pressure on the chamber side of diaphragm 18 due to the change in medication volume is only approximately one-quarter of an atmosphere.

Reservoir 14 is a closed reservoir which is completely filled with the medication and with its volume defined by reservoir wall 26 and diaphragm wall 18. Of course, the wall 18 could be designed and installed so that it expands as medication is withdrawn from the reservoir, rather than collapsing as medication is withdrawn from the reservoir, as in FIG. 2.

Medication refill port 28 has a resilient plug therebelow which is connected to the reservoir by means of port 30. Resilient plug 28 is similar to the type of plug which is used in medication bottles from which an injection is drawn. Thus, a hypodermic needle, such as on a syringe, can be thrust through the skin and through the resilient plug 28 to inject a quantity of liquid medication into the refill chamber below plug 28 and thence through port 30 to refill reservoir 14.

As is seen in FIG. 2, chamber refill port 32 communicates with chamber 16. This port also contains elastomeric material of such nature that it can be perforated by a hypodermic needle. Insertion of the needle permits exchange of fluid between the syringe and the chamber, and withdrawal of the needle permits the port to self-seal to provide closure for the chamber. Medication can be inserted and withdrawn from medication reservoir 14 by means of a hypodermic needle through medication refill port 28, while gaseous fluid can be introduced and withdrawn from chamber 16 by a needle and syringe through chamber port 32. Chamber 16 is closed from the atmosphere and from body tissue. A needle with a gage may be used to measure the pressure in the chamber to deduce the volume of remaining medication. The gas pressure is an indirect indication of the amount of liquid contained in the medication reservoir. Reservoir pressure can go above body pressure because the outlet of the reservoir terminates in tubing which is positively pinched off by the medication delivery means. Pumping action provides the necessary pressure to open the valve, regardless of reservoir pressure. The lower pressure limit in medication reservoir 14 is the limit in which the medication can be reliably pumped.

Pump lever 34 is pivoted in body 12 and is located in slot 38 in the side of the body. One end of the lever or pivoted thrustplate is in turn pivoted to the plunger 40 so that rocking of the lever causes reciprocation of the plunger. No spring return is applied so that positive rocking of the lever in either direction is required for motion of the plunger. The position of the thrustplate 34 in slot 38 in the side of the body 12 is such that only through careful palpation can the lever be found and rocked. This prevents inadvertent actuation of the plunger, and thus inadvertent medication dispensing. Flexible cover 42 over thrustplate 34 and its slot protects against tissue ingrowth and prevents leakage past plunger 40 to the body cavity. Recess 44 opposite rocking thrust lever 34 aids in location and operation of the lever.

Transfer port 46, see FIG. 2, is sealed in bore 48 and carries the entrance end of tube 50. Alternatively, a suction valve can be used. Resilient tube 50 extends around the inside of circular pump cavity 52. The tube makes contact at least one-third turn around the cavity, as shown (but more is possible), and extends out of the cavity to discharge valve 54, see FIG. 3.

Pump spider 56 carries three equally spaced rollers, one of which is seen at 56. Each roller, including roller 56, squeezes the tube 50 so that it is closed under the roller. Thus, successive volumes are located within the tube between the rollers. There is a sufficient number of rollers so that the tube is always closed in at least one location. The employment of three rollers, as described in this embodiment, causes closure of the tube at two locations at all times. Advancement of the rollers by rotation of the spider causes pumping. A ratchet wheel is fastened to the pump spider, and a pawl on plunger 40 engages in the ratchet wheel. Rocking of pivoted thrust plate 34 causes rotational advance of the pump. Thrust plate 34 is located in a side cavity 38 in body 12 so that it cannot be inadvertently actuated, but it extends out of the cavity for access. It must be positively advanced by depression thereof over plunger 40 and must be returned by pressing upon the opposite end. Under these actuation conditions, inadvertent actuation is unlikely. Cover 42 extends over cavity 38 in which the thrust plate acts. Cover 42 is resilient and provides a seal both to prevent tissue ingrowth into the cavity (which might inhibit operation of the thrust plate) and to prevent egress of medication from the implanted device should the pump tube 50 fail. Thus, cover 42 protects against both inward and outward exchange.

It is critical to this invention that the insulin be discharged onto the outside surface of the muscle tissue layer. The implantable medication-dispensing device 10 has bottom surface 58, see FIG. 3, which is designed to lie against the muscle tissue layer when device 10 is implanted. It is implanted under the skin in the loosely connected subcutaneous tissue or hypoderm. Thus, bottom surface 58 lies on top of body tissues under the skin layers. With discharge of insulin medication onto that surface, absorption takes place. This is critical, because discharge of insulin onto the skin layers does not permit ready insulin absorption. Passage 60 extends from pump wall 52 through a portion of the body 12 and extends downward to exit through the bottom surface at port 62, see FIG. 3. Tube 50 extends through the pumping area and through passage 60 to engage around outlet valve 54.

Outlet valve 54 has inlet bore 64, outlet bore 66, and cross bores 68 and 70. Resilient tube 50 (of silicone rubber) is tied around outlet valve 54 at its inlet end. It extends over cross bores 68 and 70 to act as a double check valve. Now, when insulin under pressure is provided in tube 50, it expands tube 50 around bores 68 and 70 to permit insulin passage from inlet 64, through cross bores 68 and 70, and out of outlet bore 66. This prevents dribbling of insulin from the pump between medication deliveries. Outlet bore 66 is sufficiently small so that forceful ejection is achieved. The forceful ejection displaces any plug of ingrowth. Furthermore, the double check valve construction prevents flow in either direction, except when pressure is developed by pumping. A space around outlet valve 54 in port 62 is closed by sealant 72, for example epoxy. Sealant 72 prevents medication leaks into the body, should the pump tube fail. In this way, forceful and controlled ejection is achieved. Outlet bore 66 is of sufficiently small diameter that jetlike flow occurs, even with small volumes.

This invention having been described in its preferred embodiment, it is clear that it is susceptible to numerous modifications and embodiments within the ability of those skilled in the art and without the exercise of the inventive faculty. Accordingly, the scope of this invention is defined by the scope of the following claims.

What is claimed is:

1. An implantable insulin medication-dispensing device comprising:

a substantially rigid body having a top directed toward the skin and having a bottom directed toward subcutaneous tissue when implanted and having opposed sides;

a chamber in said body having a movable diaphragm member therein to separate said chamber into an insulin reservior and gas chamber;

a refill port in the top of said body connected to said medication reservoir, said refill chamber having resilient plug to permit transcutaneous hypodermic injection of liquid insulin medication from the exterior of the device through said refill port into said reservoir;

a chamber port in the top of said body connected to said chamber, said chamber having a resilient plug to permit transcutaneous hypodermic injection of gas from the exterior of the device through said port into said gas chamber to control gas pressure in said chamber and to measure gas pressure in said chamber;

an insulin medication-dispensing pump connected to said medication volume of said reservoir to cause periodic flow of liquid insulin medication out of said reservoir when said device is actuated, said insulin medication-dispensing pump having a pump chamber having an inlet and an outlet such that actuation of said pump causes flow of liquid insulin, an outlet check valve at the outlet termination of said pump chamber outlet directed out of said bottom so that insulin discharge from said outlet check valve discharges insulin out of said medication-dispensing device directly to subcutaneous body tissue to prevent draining of the pump or pump outlet between pumping periods and prevent body tissue from growing into said dispensing pump outlet; and actuation means connected to said pump for discharging medication from said insulin dispensing device, said actuation means being a manually accessible thrustor so positioned on one of said sides of said body that said thrustor can be transcutaneously manually actuated by transcutaneously manually grasping said opposed sides and actuating said thrustor for actuating said pump for dispensing insulin into the body upon physiological demand, said insulin reservoir, said gas chamber, said refill port, said chamber port, said medication-dispensing port, and said manually accessible thrustor all being mounted in said substantially rigid body so that actuation of said pump to discharge medication does not cause reduction in external volume of said substantially rigid body as a result of reduction in insulin volume in said reservoir.

2. The implantable insulin medication-dispensing device of claim 1 wherein a palpable finger-engaging notch is provided in the side of said device opposite said actuation means so that transcutaneous manual grasping of said device comprises engagement with said notch and with said manually accessible thrustor.

3. The implantable insulin medication-dispensing device of claim 1 wherein said manually accessible thrustor is a lever having two ends which are manually accessible so that pressing one end of said lever causes advance of said pump to pump medication and depressing the other end of said lever causes resetting for subsequent advance of said pump so that said lever must be alternately actuated to cause excessive pump actuation.

4. The implantable medication-dispensing device of claim 3 wherein said lever is pivoted between its ends and said lever extends out beyond one of said sides of said device.

5. The implantable medication-dispensing device of claim 4 wherein a palpable finger-engaging notch is provided in the side of said device opposite said actuation means so that transcutaneous manual grasping of said device comprises engagement with said notch and with said manually accessible thrustor.

6. The implantable insulin medication-dispensing device of claim 1 wherein said pump is a peristaltic pump having a flexible tubing therein and said discharge check valve has a crossed bore therein, with said flexible tubing extending over said crossed bore so that pressure in said tubing expands said tubing over said crossed bore to permit flow of medication from said tubing through said outlet check valve, said outlet check valve being located in a port in said bottom of said device.

7. The implantable insuling medication-dispensing device of claim 6 wherein said outlet check valve has an inlet bore in communication with said tube, and first and second cross bores and an outlet bore, said first cross bore being in communication with said inlet bore and said second cross bore being in communication with said outlet bore, said flexible tubing covering both of said cross bores so that insulin under pressure flows from said inlet bore, through said first cross bore, inside the expanded tubing, and to said second cross bore and thence jets out of said outlet bore into tissue below the skin.

8. The implantable medication-dispensing device of claim 1 wherein said movable member in said chamber is a resilient diaphragm separating the liquid medication-containing reservoir from the closed gas chamber, said diaphragm flexing as medication is withdrawn from the medication-containing portion of said reservoir for dispensing.

* * * * *